(12) United States Patent
Sih et al.

(10) Patent No.: US 6,316,645 B1
(45) Date of Patent: Nov. 13, 2001

(54) SYNTHESIS OF CONJUGATED POLYUNSATURATED FATTY ACIDS

(75) Inventors: Charles J. Sih; Chien-An Chen, both of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/175,793

(22) Filed: Oct. 20, 1998

(51) Int. Cl.$^7$ .................................................. C07C 51/347
(52) U.S. Cl. ............................ 554/126; 554/223; 554/224
(58) Field of Search ....................... 554/126, 223, 554/224

(56) References Cited

U.S. PATENT DOCUMENTS

| | | |
|---|---|---|
| 4,164,505 | 8/1979 | Kraja . |
| 4,381,264 | 4/1983 | Struve . |
| 5,430,066 | 7/1995 | Cook et al. . |
| 5,472,727 | 12/1995 | Campbell et al. . |
| 5,504,114 | 4/1996 | Cook et al. . |
| 5,554,646 | 9/1996 | Cook et al. . |
| 5,756,143 | 5/1998 | Cain et al. . |

FOREIGN PATENT DOCUMENTS

| | | | |
|---|---|---|---|
| WO 97/18320 | 5/1997 | (WO) . | |
| 97/18320 | * 5/1997 | (WO) | ................................ C12P/7/64 |

OTHER PUBLICATIONS

Kass, J.P. et al., "Pseudo–eleosteric Acid" *J. Am. Chem. Soc.* vol. 61 (1939) 3292–3294.

Kepler, Carol R. et al. "Intermediates and Products of the Biohydrogenation of Linoleic Acid by *Butyrivibrio fibrosolvens*" *J. Biol. Chem.* vol. 241 (1966) 1350–1354.

Mounts, T.L. et al., "Conjugation of Polyunsaturated Acids" *Lipids*, vol. 5 (1970) 997–1005.

(List continued on next page.)

*Primary Examiner*—Deborah D. Carr
(74) *Attorney, Agent, or Firm*—Michael Best & Friedrich LLP; Teresa J. Welch

(57) ABSTRACT

The present invention provides a method of preparing conjugated polyunsaturated fatty acids wherein the fatty acid substrate has two or more double bonds and diallylic hydrogens by one or more treatments with a superstrong base. Isomeric purity can be accomplished with a further step of enzymatic hydrolysis and separation.

22 Claims, 3 Drawing Sheets

OTHER PUBLICATIONS

Nichols, Jr., Peter et al. "Isomers of Conjugated Fatty Acids. I. Alkali–isomerized Linoleic Acid" *J. Am. Chem. Soc.* vol. 73 (1951) 247–253.

Privett, O.S. et al., "Determination of the Specific Positions of cis and trans Double Bonds in Polyenes" Lipids, vol. 1 (1966) 98–103.

Schlosser, Manfred "Superbases for organic synthesis" *Pure & Appl. Chem.* vol. 60 (1988) 1627–1634.

Schlosser, von Manfred, et al., "Regioselective Metalation of Phenylcyclopropane and Smooth Addition of I–Phenyl-cyclopropyl Potassium onto Ethylene" *Helvetica Chimica Acta Col.* 63 (1980) 2404–2410.

Sehat, Najibullah et al., "Silver–Ion High–Performance Liquid Chromatographic Separation and Identification of Conjugated Linoleic Acid Isomers" *Lipids* vol. 33 (1998) 217–221.

Steinhart, Carol "Conjugated Linoleic Acid–The Good News about Animal Fat" *J. Chem. Ed.* vol. 73 (1996) A302–A303.

"Isomers in Commercial Samples of Conjugated Linoleic Acid" *J. Am. Oil Chem. Soc.* vol. 74 (1997) 1231.

Berdeaux, O. et al. "Large–Scale Synthesis of Methyl cis–9, trans–11–Octadecadienoate from Methyl Ricinoleate" *J. Am. Oil Chem. Soc.* vol. 74 (1997) 1011–1015.

"Scientific forum explores CLA knowledge" INFORM, vol. 9:1 (1998) 69–72.

"Conjugated linoleic acid offers research promise" INFORM, vol. 7:2 (1996) 152–159.

Sreenivasan, B., et al., "Isomerization of Linoleic, Linolenic, and Other Polyunsaturated Acids with Potassium Tertiary Butoxide and Its Application in the Spectrophotometric Estimation of These Acids", *Journal of the American Oil Chemists' Society*, vol. 33, No. 11 (Nov. 11, 1956) pp. 521–526.

Schlosser, M., et al., "2–Methylpentadienyl–and 2,4–Dimethylpentadienylpotassium: First Examples of U–Shaped, through Open–Chain, Organometallics", *Journal of the American Chemical Society*, vol. 100, No. 10, (May 10, 1978) pp. 3258–3260.

Chen, C., et al., "Chemoenzymatic Synthesis of Conjugated Linoleic Acid", *Journal of Organic Chemistry*, vol. 63, No. 26, (Dec. 25, 1998) pp. 6920–6921.

Mounts et al, Conjugation of Polyunsaturated Acids, department of Chemistry, Bradley University, Lipids vol. 5 No. 12., 1970.*

Garcia et al, Enrichment of butteroil with conjugated linoleic acid via enzymatic interesterification (acidolysis) reactions, Apr. 1998.*

* cited by examiner

SYNTHESIS OF CONJUGATED POLYUNSATURATED FATTY ACIDS

STATEMENT REGARDING FEDERALLY SPONSORED RESEARCH OR DEVELOPMENT

This invention was made with Government support under Grant No. GM33149 awarded by the National Institutes of Health. The U.S. Government has certain rights in this invention.

CROSS-REFERENCE TO RELATED APPLICATIONS

Not Applicable

BACKGROUND OF THE INVENTION

This invention relates generally to conjugated fatty acids and, in particular, to a method of making such conjugated fatty acids and isolating specific isomers thereof.

In recent years, substantial interest has arisen in conjugated polyunsaturated fatty acids, especially conjugated linoleic acid. Polyunsaturated fatty acids are those fatty acids that have two or more double bonds between carbon atoms in their hydrocarbon chain. These acids are usually vegetable-derived and consist of hydrocarbon chains of 18 or more carbon atoms. Of these acids, linoleic, linolenic and arachidonic acid are the so-called essential fatty acids.

The positioning of the double bonds in the hydrocarbon chain is typically not in a conjugated, i.e., alternating double bond-single bond-double bond, manner. For example, linoleic acid is an octadecadienoic fatty acid having an eighteen carbon chain with two double bonds (18:2), one between carbons 9 and 10 and one between carbons 12 and 13, in which the configuration about each double bond is the cis configuration, i.e., cis-9,cis-12-octadecadienoic acid (or c9,c12-octadecadienoic acid). Linolenic acid is also an eighteen carbon acid but with three double bonds (18:3) at carbons 9, 12 and 15 in which all three double bonds have in the cis configuration, i.e., c9,c12,c15-octadecadienoic acid. Changing the position of the double bonds, e.g., conjugation, gives rise to many positional and geometric (i.e., cis-trans) isomers.

Conjugated linoleic acid (CLA) is a collective term for positional and geometric isomers of linoleic acid having a conjugated double-bond system starting at carbon 9, 10 or 11. For example, one CLA positional isomer has double bonds between carbons 9 and 10 and carbons 11 and 12 (i.e, 9,11-octadecadienoic acid); another has double bonds between carbons 10 and 11 and carbons 12 and 13 (i.e., 10,12-octadecadienoic acid), each with several possible cis and trans isomers. Because of cis/trans isomerism, the 9,11 and 10,12 CLA's can have eight geometric different isomers, i.e., cis-9, cis-11; cis-9,trans-11; trans-9,cis-11; trans-9,trans-11; cis-10,cis-12; cis-10,trans-12; trans-10,cis-12 and trans-10, trans-12.

Although a conjugated structure is not usual in fatty acids, the existence of CLA has been known for many years, and CLA is found naturally in milk, dairy products and meat for ruminants because of its formation as an intermediate of biohydrogenation by anaerobic bacteria in the rumen. The cis-9,trans-11 and the trans-10,cis-12 isomers appear to be the most abundant isomers.

The cis-9,trans-11 isomer has been shown to be the first intermediate in the biohydrogenation of linoleic acid by the anaerobic rumen bacterium *Butyrvibrio fibrisolvens*. This reaction is catalyzed by the enzyme linoleate isomerase which converts the cis-12 double bond of linoleic acid to a trans-11 double bond. (C. R. Kepler et al., 241 *J. Biol. Chem.* (1966) 1350.) It has also been found that the normal intestinal flora of rats can convert linoleic acid to the cis-9,trans-11 isomer. The reaction does not, however, take place in animals lacking the required bacteria. Therefore, CLA is largely a product of microbial metabolism in the digestive tract of primarily ruminants, but to a lesser extent in other mammals and birds.

Interest in CLA has increased because of reports that dietary CLA reduces carcinogenesis, atherosclerosis and body fat in laboratory animals (see, e.g., B. F. Haumann, 1 *Inform* (1996) 152; C. Steinhart, 73 *J. Chem. Ed.* (1996) A302). To date, there is no conclusive evidence as to which isomer or isomers of the many CLA isomers is the active component(s). However, it is generally assumed that the active isomer is the major isomer, i.e., the cis-9,trans-11 isomer, found in dairy products. Whether eaten in the diet or synthesized in the digestive tract, CLA is absorbed from the gut and distributed throughout the body wherein the cis-9, trans-11 isomer is incorporated into blood lipids, cell membranes and fat tissue.

CLA has been found to be an in vitro antioxidant, and in cells, it protects membranes from oxidative attack. In relation to other important dietary antioxidants, it quenches singlet oxygen less effectively than β-carotene but more effectively than α-tocopherol. It appears to act as a chain terminating antioxidant by chain-propagating free radicals.

Currently, commercial sources of CLA are produced by alkaline isomerization of linoleic acid, i.e., by heating linoleic acid with sodium hydroxide in ethylene glycol at high temperatures. Commercial samples so produced yield complex mixtures of many different isomers. (P. I. Nichols, Jr. et al., 73 *J. Am. Chem.* (1951) 247.) In a recent report (N. Sehat et al., 33 *Lipids* (1998) 217), using silver-ion impregnated high performance liquid chromatography, a commercial sample of CLA was separated into twelve separate peaks. Other methods of preparation have been reported; see, e.g., U.S. Pat. No. 4,381,264 issued to Struve which utilizes sulfur dioxide in the presence of soap-forming bases but appears to produce primarily trans-trans conjugated fatty acids; U.S. Pat. No. 4,164,505 issued to Krajca which discloses a flow process for conjugating unsaturation of fatty acids using alkali metal hydroxides; WO 97/18320, a PCT published application disclosing a process for the preparation of materials with a high content of long chain polyunsaturated fatty acids; Mounts et al.; 5 *Lipids* 997 (1970). As some of the isomers may give rise to undesirable side effects (namely, 11,13 isomers), an alternative method that affords only the desirable isomers is clearly warranted.

Conjugation of linolenic acid with its three double bonds affords the possibility of two conjugated double bond systems; namely, conjugated diene isomers and conjugated triene isomers. The conjugated diene isomers are essentially CLA equivalents. A conjugated triene isomer, pseudo-eleostearic acid, 10,12,14-octadecadienoic acid, has long been reported, formed by partially converting linolenic acid with alcoholic alkalies (Kass and Burr, 61 *J. Am. Chem. Soc.* (1939) 3292).

Despite recognition of the need for isomeric purity of CLA and other conjugated fatty acids, the prior art has produced very little in the way of a practical technique for such synthesis and isomeric separation.

BRIEF SUMMARY OF THE INVENTION

The present invention provides a method of preparation of conjugated polyunsaturated fatty acids. The conjugated fatty acids are suitably conjugated diene and conjugated triene fatty acids. Conjugated diene fatty acids include conjugated linoleic acid (CLA) and conjugated diene linolenic acid. Conjugated triene fatty acids include fully conjugated linolenic acid. The method of the present invention is carried out under relatively mild conditions compared to the refluxing conditions of the currently used alkaline isomerization.

The foregoing, and other advantages of the present invention, are realized in its most general aspect thereof in method comprising the steps of deprotonating a polyunsaturated fatty acid with a superstrong base, e.g., pK>30, and then reprotonating the fatty acid to yield the desired conjugated isomers. The polyunsaturated fatty acid substrate has two or more double bonds in its hydrocarbon chain. The deprotonating step selectively removes diallylic hydrogens from the fatty acid, and is carried out at low temperature. The reprotonating step is accomplished with reaction with a strong acid. Isomeric purity can then be achieved by reaction of the conjugated isomers with a regioselective lipase that can discriminate between isomers to yield the substantially pure desired conjugated isomer.

In an illustrated embodiment, the invention provides a method of preparing stereospecific isomers of linoleic acid, including deprotonating linoleic acid with the superstrong base, and then reprotonating it to substantially yield only two major isomers, cis-9,trans-11 and cis-12,trans-10. These isomers are then treated with a regioselective lipase to yield the cis-9,trans-11 isomer, substantially free of the cis-12,trans-10 isomer.

In another illustrated embodiment, the invention provides a method for preparing conjugated linolenic acid, including deprotonating linolenic acid with the superstrong base and reprotonating it to yield four conjugated diene isomers, cis-9,trans-13,cis-15; cis-9,trans-11,cis-15; cis-9,cis-12,trans-14; and trans-10,cis-12,cis-15. The latter two isomers, possessing diallylic hydrogens, are then again deprotonated with the superstrong base to yield the conjugated triene linolenic acid isomer, trans-10,cis-12,trans-14.

The most suitable bases for deprotonation include but are not limited to sec-butyllithium; a Schlosser base such as n-butyllithium/potassium tert-butoxide, and trimethylsilylmethyl potassium.

The regioselective lipase includes but is not limited to *Aspergillus niger* lipase, *Candida antarctica* lipase and *Geotrichum candidum* lipase.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWING(S)

The preferred exemplary embodiment of the present invention will hereinafter be described in conjunction with the appended drawing wherein like designations refer to like elements throughout and in which.

DETAILED DESCRIPTION OF THE INVENTION

Figure 1:
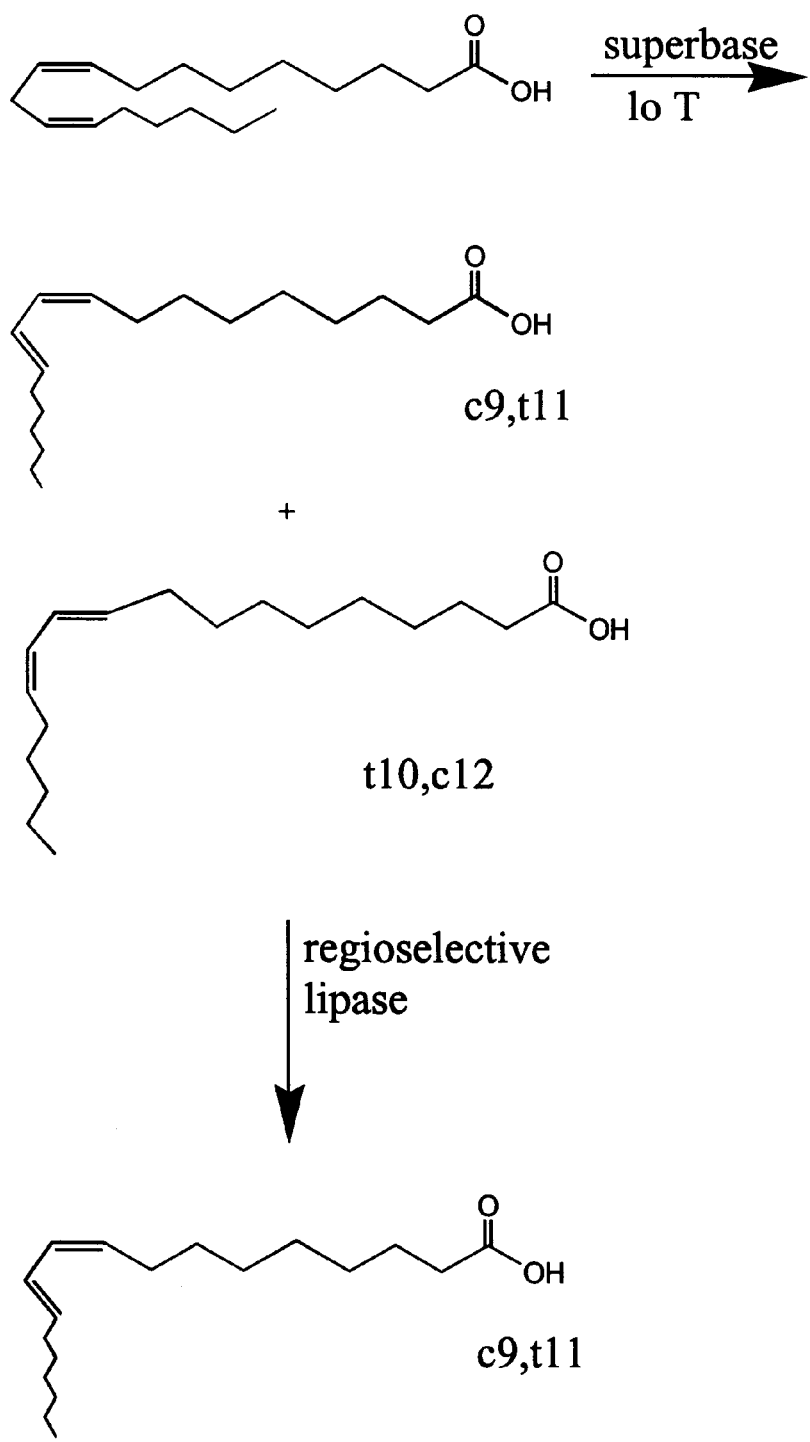
FIG. 1 is a reaction scheme for the preparation of stereospecific isomers of linoleic acid.

The present invention relates broadly to a method of preparing conjugated polyunsaturated fatty acids. The method of the present invention is particularly useful in preparing certain isomers of linoleic and linolenic acids. Accordingly, the present invention will now be described in detail with respect to such endeavors; however, those skilled in the art will appreciate that such a description of the invention is meant to be exemplary only and should not be viewed as limitative on the full scope thereof.

The method of the present invention is characterized by an ability to yield conjugated diene and conjugated triene polyunsaturated fatty acids as well as provide certain geometric isomers of conjugated polyunsaturated fatty acids in substantial isomeric purity. These attributes are achieved through a novel combination of synthetic steps.

In the following description of the method of the invention, process steps are carried out at room temperature and atmospheric pressure unless otherwise specified. As used herein, the letter "c" is used to abbreviate the term "cis" and the letter "t" is used to abbreviate the term "trans" in reference to geometric isomers, e.g., c9,t11 means a double bond at carbon-9 which has the cis configuration and a double bond at carbon 11 with the trans configuration. The terms "substantially pure" or "substantially free" in reference to isomers means a purity of at least 85%. The term "conjugated diene" refers to a hydrocarbon chain in which there are two carbon-carbon double bonds separated by a single carbon-carbon bond. The term "conjugated triene" refers to a hydrocarbon chain in which there are three carbon-carbon double bonds and each double bond is separated from the next by a single carbon-carbon bond, i.e., an alternating bonding pattern of double bond, single bond, double bond, single bond, double bond. The term "superstrong base" or "superbase" refers to a base that has a pK>30. The term "regioselective" in reference to a lipase refers to a specificity or preference for hydrolyzing or esterifying a specific unsaturation, e.g., c9,t11.

In its most general aspect, the invention provides a method of preparation of conjugated polyunsaturated fatty acids. The method includes conjugation of the double bonds of polyunsaturated fatty acids by a deprotonation/reprotonation step to yield conjugated diene isomers of the starting fatty acid substrate, followed by a subsequent stereoselective hydrolysis to yield particular isomers. The fatty acid substrate suitably has two or more double bonds. For fatty acids that have more than two double bonds, e.g., three double bonds, the deprotonation/reprotonation step can be repeated to yield fully conjugated isomers. The deprotonation is accomplished by treatment with a superstrong base at low temperature in an organic solvent in contrast to the conventional alkaline isomerism which must be carried out at high temperature (e.g., ~150° C. to 260° C.). Reprotonation is suitably carried out by quenching the deprotonation with a strong acid such as hydrochloric acid (HCl), sulfuric acid, citric acid and oxalic acid.

Stereoselective hydrolysis or esterification is accomplished by treatment with a regioselective lipase, such as *Aspergillus niger* lipase, *Candida antarctica* lipase or *Geotrichum candidum* lipase. For example, *aspergillus niger* preferentially utilizes the c9,t10 isomer either via hydrolysis of the methyl ester in buffer or via esterification in aqueous n-butanol. *Candida antarctica* preferentially attacks the c10,t12 isomer.

Fatty acids that are suitably conjugated in accordance with the present invention include, but are not limited to, linoleic acid, linolenic acid, γ-linolenic acid, 8,11-eicosadienoic acid, 8,11,14-eicosatrienoic acid, 11,14,17-eicosatrienoic acid and arachidonic acid.

Figure 2:
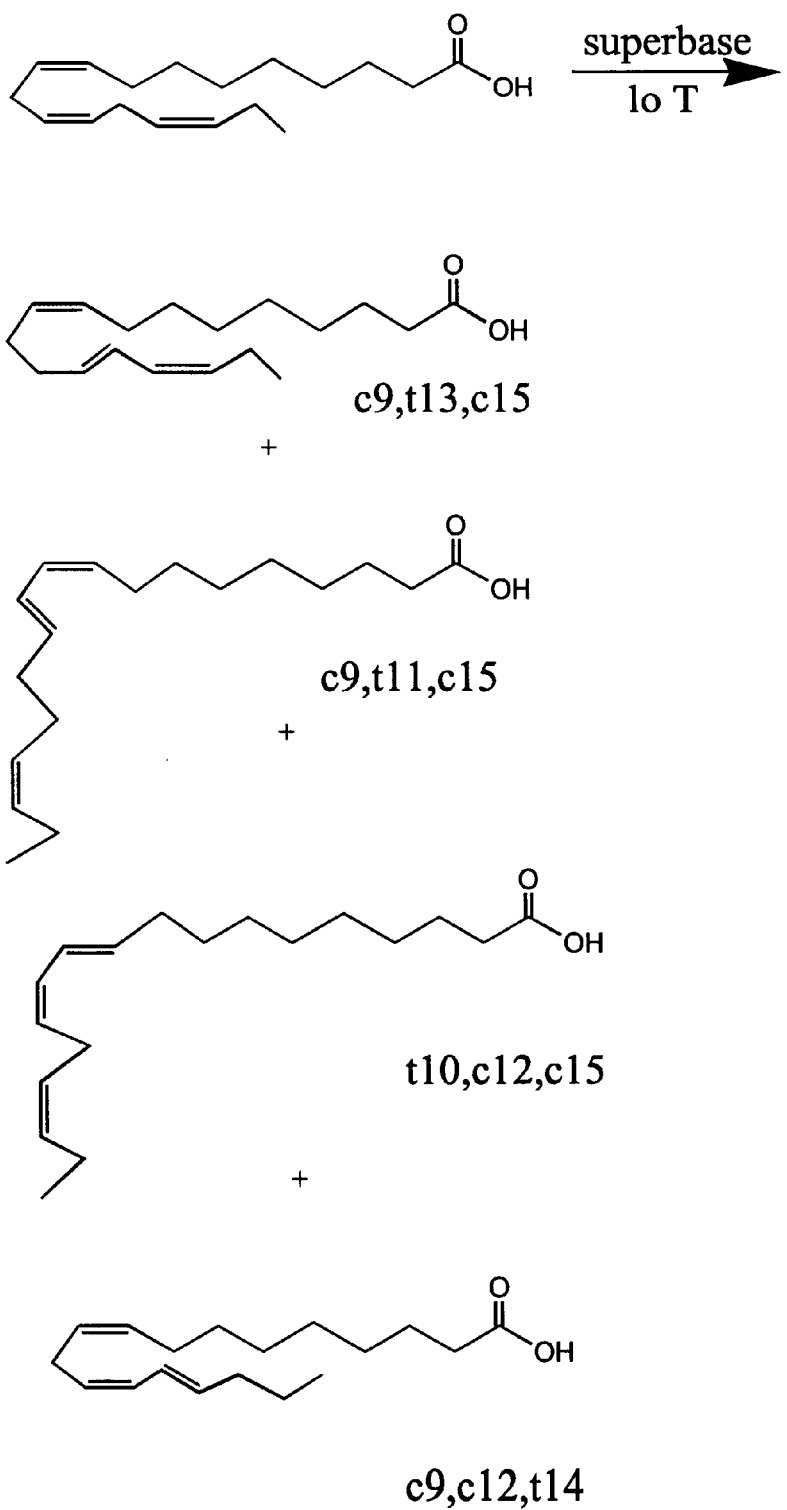
FIG. 2 is a reaction scheme for the preparation of isomers of linolenic acid to form conjugated diene isomers.
Figure 3:
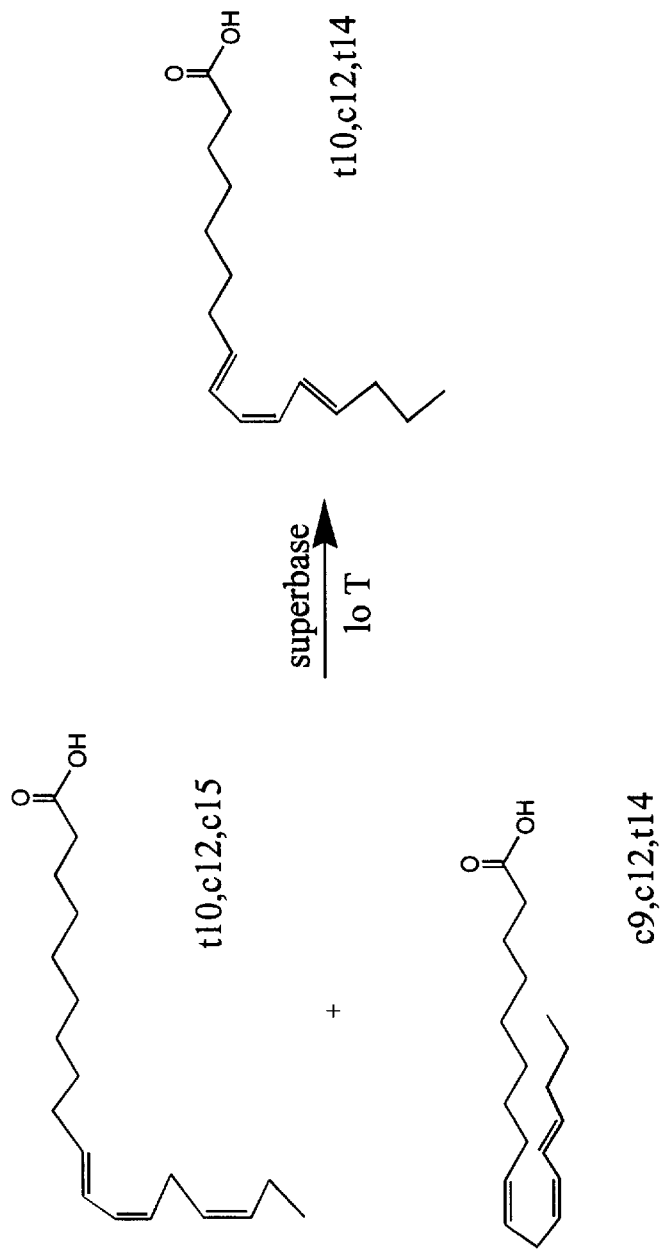
FIG. 3 is a reaction scheme for the preparation of a specific conjugated triene isomer of linolenic acid.

The synthesis in accordance with the present invention is accomplished according to the representative schema presented in FIGS. 1 and 2. FIG. 1 illustrates a synthetic scheme for conjugated linoleic acid (CLA). Specifically, linoleic acid is deprotonated in a suitable organic solvent with a superstrong base at a low temperature as long as the base does not react with the organic solvent. After a period of time, the reaction is quenched by pouring the reaction mixture into an acidic solution such as HCl for reprotonation and conversion to the methyl esters with diazomethane to yield a mixture of the c9,t11 and c12,t10 isomers in about a 3:2 ratio plus about 5–10% unconjugated isomers and residual linoleic acid. Pure c9,t11 CLA is obtained by subjecting the reaction mixture of CLA methyl esters (c9,t11 and c12,t10) to stereoselective hydrolysis using a regioselective lipase, i.e., an enzyme that has a unique specificity for fatty acids containing c9,t11 or t10,c12 unsaturation. (See, e.g., R. G. Jensen, 9 *Lipids* (1974) 149, incorporated herein by reference.) The lipase action converts the c9,t11 methyl ester to the acid form and permits separation of the acid from the t10,c12 ester.

The reaction mixture after quenching, i.e., as with HCl, can be worked up in a number of ways including removal of the organic solvent, extraction of the CLA into hexane or other suitable organic solvent, drying over sodium sulfate and evaporation to dryness under reduced pressure.

The presence of the major isomers of CLA after the deprotonation/reprotonation was confirmed by subjecting reaction mixture to silver-ion high pressure liquid chromatography (HPLC) according to the method of Sehat et al., supra, incorporated herein by reference. Such $Ag^+$-HPLC resulted in the presence of only two peaks, which were identified as the c9,t11; c12,t10 isomers of CLA plus some residual linoleic acid, which can be detected in a proton NMR spectrum. The position of the double bonds in these regioisomers can be determined according to the method of Privett and Nickell (O. S. Privett and E. C. Nickell, 1 *Lipids* (1966) 98), incorporated herein by reference).

A variety of organic solvents are suitable as the solvent for the reaction in accordance with the present invention, especially the ethereal solvents such as tetrahydrofuran (THF), tetrahydropyran, isopropyl ether, propyl ether, butyl ether, dimethoxyethane and 2,3-dimethoxypropane. The superstrong base is preferably selected from the group consisting of sec-butyllithium, a Schlosser base; namely, n-butyllithium/potassium tert-butoxide (Schlosser, 60 *Pure & Appl. Chem.* 1627 (1988), incorporated herein by reference), and trimethylsilylmethyl potassium. The concentration of fatty acid suitably ranges from 0.05 to 3M, preferably 0.1 to 2 M, as long as the reaction mixture remains in solution. The lipase is suitably selected from the group consisting of *Aspergillus niger* lipase, *Candida antarctica* lipase and *Geotrichum candidum* lipase.

The temperature for conjugation under the conditions according to the present invention lies between –78° C. and –10° C., preferably about –40° C. to –78° C. The reaction time is generally between about 15 min and 60 min, typically about 30 min.

FIG. 2 illustrates a scheme for preparing conjugated linolenic acid. Specifically, linolenic acid is subjected to a deprotonation/reprotonation using a superstrong base as described hereinabove to yield four conjugated diene geometric isomers, cis-9,trans-13,cis-15; cis-9,trans-11,cis-15; cis-9,cis12,trans-14; and trans-10,cis-12,cis-15. The latter two isomers having diallylic hydrogens are subject to a second deprotonated/reprotonated using the superstrong base to yield the conjugated triene, trans-10,cis-12,trans-14. Solvents, superstrong bases, concentration ranges and reaction conditions are suitably as described hereinabove.

The compounds of the invention are considered to have pharmaceutical value similar to CLA.

The present invention is further explained by the following examples which should not be construed by way of limiting the scope of the present invention.

EXAMPLE 1

Preparation of c9,t11 and t10,c12 CLA Isomeric Mixture Using Schlosser Base

To a –78° C. solution of n-butyllithium (14.2 mL of a 2.5 M solution in hexane, 35.5 mmol) in THF (150 mL) was added potassium tert-butoxide (35.4 mL of a 1 M solution in THF, 35.4 mmol). After 5 min, a solution of linoleic acid (3.1 g, 11.1 mmol) in THF (10 mL+10 mL) was added. The resulting solution was stirred at –78° C. for another 30 min and poured into 150 mL 6N HCl at 0° C. The aqueous layer was extracted with ether (150 mL×3) and the combined organic layers were washed with a saturated sodium chloride solution, dried over magnesium sulfate, filtered and concentrated under reduced pressure.

The crude products were dissolved in anhydrous diethyl ether (45 mL) and methanol (5 mL). To this solution was added diazomethane (ether solution) until the solution turned yellow and the mixture was stirred at room temperature for 30 min. to yield the methyl esters. Excess diazomethane was evaporated with a stream of nitrogen, and the reaction was concentrated in vacuo. Purification of the crude products by $AgNO_3$-silica gel chromatography using hexane/ethyl acetate (60:1) as eluent gave a mixture of c9,t11 and t10,c12 CLA methyl ester isomers 2.5 g (77%). Analysis of this mixture using silver-ion impregnated HPLC as described by Sehat et al., supra, showed the presence of only two peaks in a ratio of 1.0:1.5 corresponding to the retention times of t10,c12 and c9,t11 CLA methyl esters, respectively.

EXAMPLE 2

Separation of the c9,t11 CLA Isomer using Geotrichum Candidum Lipase

Lipase GC-4 (*Geotrichum Candidum* Amano, 25.7 mg) dissolved in phosphate buffer (4 mL, pH 7.0, 0.1M) was stirred at room temperature for 5 min. To this mixture was added 24 mg of c9,t11 and t10,c12 CLA-methyl ester isomers in 0.24 mL of acetone, and the resulting solution was stirred at room temperature for 8 hours. After acidification of the mixture with 10% HCl, the aqueous layer was extracted with ether (10 mL×3), and the combined organic extracts were washed with a saturated sodium chloride solution and then dried over magnesium sulfate. Removal of solvent and chromatography on silica gel using ethyl acetate/hexane (30:1) as the eluent, followed by elution of the column with methanol/methylene chloride (5:95), gave c9,t11 CLA (10.7 mg) along with c9,t11 and t10,c12 CLA-methyl ester mixtures (11.6) mg).

EXAMPLE 3

Preparation of c9,t11 and t10,c12 CLA Isomeric Mixture using Sec-butyllithium

To a –60° C. solution of linoleic acid (1.1 g, 3.9 mmol) in THF (10 mL) was added sec-butyllithium (9.6 mL of a 1.3 M solution in cyclohexane, 12.5 mmol). After 5 min, the temperature was allowed to rise to –40° C. and stirred for another 30 min at this temperature. The resulting solution was poured into 10 mL 6N HCl at 0° C. The aqueous layer was extracted with ether (10 mL×3), and the combined organic layers were washed with a saturated sodium chloride solution, dried over magnesium sulfate and filtered. The solvent was removed by rotary evaporation and gave the crude product (1.1 g) which contain 55% of c9,t11 and t10,c12 CLA isomers.

EXAMPLE 4

Preparation of c9,t11 CLA Isomer using *Aspergillus niger* Lipase

To a solution of c9,t11 and t10,c12 CLA-methyl ester isomers (21.6 mg) in phosphate buffer (2 mL, pH 7.0, 0.1 M) was added lipase APF-12 (*Aspergillus niger*, Amano, 4.4 mg). After stirring at room temperature for 3 hours, the mixture was acidified with 10% HCl (2 mL) and extracted with ether (5 mL×3). The combined organic layers were washed with a saturated sodium chloride solution and dried over magnesium sulfate. Removal of solvent and chromatography on silica gel using ethyl acetate/hexane (30:1) as the eluent, followed by elution of the column with methanol/methylene chloride (5:95) gave t10,c12/c9,t11 CLA (13:87, 46% conversion) along with t10,c12/c9,t11 CLA-methyl ester (82:18).

EXAMPLE 5

Preparation of c9,t11 CLA Butyl Ester using *Aspergillus niger* Lipase

To a solution of c9,t11 and t10,c12 CLA isomers (18.8 mg) in phosphate buffer (20 μL, pH 7.0, 0.1 M) was added 1-butanol (20 μL) followed by lipase APF-12 (*Aspergillus niger*, Amano, 1 mg). After stirring at room temperature for 2.5 hours, the mixture was acidified with 10% HCl (1 mL) and extracted with ether (3 mL×3). The combined organic layers were washed with a saturated sodium chloride solution, dried over magnesium sulfate, filtered and concentrated under reduced pressure. The crude products were dissolved in anhydrous diethyl ether (5 mL) and methanol (1 mL). To this solution was added diazomethane (ether solution) until the solution turned yellow, and the mixture was stirred at room temperature for 30 min. Excess diazomethane was evaporated with a stream of nitrogen and the reaction was concentrated in vacuo. Analysis of this mixture using silver-ion impregnated HPLC as described by Sehat et al., supra, showed the presence of t10,c12/c9,t11 CLA-butyl esters (5:95, 29% conversion) and t10,c12/c9,t11 CLA-methyl esters in a ratio of 69:31.

EXAMPLE 6

Preparation of c9,t11 CLA Butyl Ester using *Candida antarctica* Lipase

To a solution of c9,t11 and t10,c12 CLA isomers (22.2 mg) in 1-butanol (40 μL) was added lipase *Candida antarctica* (Novozym 435, 1 mg). After shaking at 35° C. for 6.5 hours, the mixture was filtered and concentrated under reduced pressure. The crude products were dissolved in anhydrous diethyl ether (5 mL) and methanol (1 mL). To this solution was added diazomethane (ether solution) until the solution turned yellow, and the mixture was stirred at room temperature for 30 min. Excess diazomethane was evaporated with a stream of nitrogen, and the reaction was concentrated in vacuo. Analysis of this mixture using silver-ion impregnated HPLC as described by Sehat et al., supra, showed the presence of t10,c12/c9,t11 CLA-butyl esters in a ratio of 46:54 (55% conversion) and t10,c12/c9,t11 CLA-methyl esters in a ratio of 22:78.

EXAMPLE 7

Preparation of Conjugated Diene Linolenic Acid Isomers using Schlosser Base

To a −78° C. solution of n-butyllithium (0.16 mL of a 2.5 M solution in hexane, 0.4 mmol) in THF (1 mL) was added potassium tert-butoxide (0.4 mL of a 1 M solution in THF, 0.4 mmol). After 5 min, a solution of linolenic acid (37 mg, 0.13 mmol) in THF (1 mL) was added. The resulting solution was stirred at −78° C. for another 30 min and poured into 2 mL 1 N HCl at 0° C. The aqueous layer was extracted with ether (2 mL×3), and the combined organic layers were washed with a saturated sodium chloride solution, dried over magnesium sulfate, filtered and concentrated under reduced pressure. The crude products were dissolved in anhydrous diethyl ether (0.45 mL) and methanol (0.5 mL). To this solution was added diazomethane (ether solution) until the solution turned yellow, and the mixture was stirred at room temperature for 30 min. Excess diazomethane was evaporated with a stream of nitrogen, and the reaction was concentrated in vacuo. Analysis of this mixture using silver-ion impregnated HPLC as described by Sehat et al., supra, showed the presence of t10,c12,t14 conjugated diene methyl ester (monitored at 270 nm; retention time was 11.91 min) and c9,c12,t14; t10,c12,c15; c9,t13,c15 and c9,t11,c15 conjugated diene methyl esters (monitored at 233 nm; retention times were: 16.03 min, 16.49 min, 24.14 min, 24.59 min).

EXAMPLE 8

Preparation of Conjugated Diene Linolenic Acid Isomers using Sec-butyllithium

To a −47° C. solution of linolenic acid (92 mg, 0.33 mmol) in THF (1 mL) was added sec-butyllithium (0.89 mL of a 1.3 M solution in cyclohexane, 1.16 mmol). After 50 min, the resulting solution was poured into 3 mL 1 N HCl at 0° C. The aqueous layer was extracted with ether (3 mL×3), and the combined organic layers were washed with a saturated sodium chloride solution, dried over magnesium sulfate and filtered. Analysis of this mixture using silver-ion impregnated HPLC as described by Sehat et al., supra, showed the presence of t10,c12,t14 conjugated diene methyl esters (monitored at 270 nm; retention time was 11.91 min) and c9,c12,t14; t10,c12,c15; c9,t13,c15 and c9,t11,c15 conjugated diene methyl esters (monitored at 233 nm; retention times were: 16.03 min, 16.49 min, 24.14 min, 24.59 min).

EXAMPLE 9

Preparation of Conjugated Triene-t10,c12,t14-octaderatrienoic Acid

To a −78° C. solution of n-butyllithium (0.08 mL of a 2.5M solution in hexane, 0.2 mmol) in THF (0.5 mL) was added potassium tert-butoxide (0.2 mL of a 1M solution in THF, 0.2 mmol). After 5 min, a solution of a mixture of c9,c12,t14 and t10,c12,c15-octadecadienoic acid (18 mg, 0.063 mmol) in THF (0.5 mL) was added. The resulting solution was stirred at −78° C. for another 30 min and poured into 2 mL of 1N HCl at 0° C. The extraction, methyl ester formation and HPLC analysis was followed as described in Example 7, and yielded t10,c12,t14-actadecatrienoic acid.

In summary, the present invention provides a method of preparing conjugated polyunsaturated fatty acids wherein the fatty acid substrate has two or more double bonds and diallylic hydrogens by one or more treatments with a super-strong base. Isomeric purity can be accomplished with a further step of enzymatic hydrolysis and separation.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

What is claimed is:

1. A method for conjugation of the double bonds of polyunsaturated fatty acids comprising the steps of
   (a) deprotonating a polyunsaturated fatty acid with a superstrong base selected from the group consisting of sec-butyl lithium, a Schlosser base, and trimethylsilylmethyl potassium, and
   (b) reprotonating the fatty acid to yield conjugated fatty acid isomers.

2. The method of claim 1 further comprising the step of:
   (c) reacting the conjugated fatty acid isomers with a regioselective lipase.

3. The method of claim 1 wherein the fatty acid has more than two double bonds, the conjugated isomers are conjugated diene fatty acid isomers, and wherein steps (a) and (b) are repeated on the conjugated diene fatty acid isomers to yield conjugated triene fatty acid isomers.

4. The method of claim 1 wherein the method is carried out in the presence of an organic solvent.

5. The method of claim 1 wherein step (b) is carried out with a strong acid.

6. The method of claim 1, wherein said Schlosser base is n-butyllithium/potassium tert-butoxide.

7. The method of claim 2 wherein the product of step (c) comprises a c9,t11 conjugated fatty acid isomer.

8. The method of claim 2 wherein said lipase is selected from the group consisting of *Aspergillus niger* lipase, *Candida antarctica* lipase and *Geotrichum candidum* lipase.

9. The method of claim 8 wherein said lipase is *Aspergillus niger* lipase or *Candida antarctica* lipase.

10. The method of claim 1 wherein said reaction temperature for step (a) is in the range of −78° C. to −20° C.

11. The method of claim 1, wherein said organic solvent is selected from the group consisting of tetrahydrofuran, tetrahydropyran, isopropyl ether, propyl ether, butyl ether, dimethoxyethane, and 2,3-dimethoxypropane.

12. The method of claim 1 wherein said fatty acid is an octadecadienoic acid or an octadecadienoic acid.

13. The method of claim 12 wherein said octadecadienoic acid is linoleic acid.

14. The method of claim 12 wherein said octadecadienoic acid is linolenic acid.

15. A method for preparing c9,t11 conjugated polyunsaturated fatty acids, comprising the steps of
   (a) deprotonating a polyunsaturated fatty acid with a strong base in the presence of an organic solvent at a temperature of about −40° C. to about −78° C., the strong base being selected from sec-butyllithium, Scholosser base, and trimethylsilylmethyl potassium;
   (b) quenching step (a) and reprotonating the fatty acid with a strong acid to yield a reaction mixture of conjugated fatty acid isomers; and
   (c) treating the reaction mixture with a regioselective lipase and separating the reaction products, the lipase being selected from *Aspergillus niger* lipase, *Candida antarctica* lipase, and *Geotrichum candidum* lipase.

16. A method of preparing conjugated polyunsaturated free fatty acids, comprising the steps of treating a mixture comprising isomers of a conjugated polyunsaturated fatty acid ester with a regioselective lipase selected from the group consisting of *Aspergillus niger* lipase and *Candida antarctica* lipase to yield conjugated polyunsaturated free fatty acids comprising c9,t11 free fatty acid isomer.

17. A method of preparing conjugated polyunsaturated fatty acids, comprising the steps of deprotonating a polyunsaturated fatty acid having diallylic hydrogens with a superstrong base in an organic solvent at a temperature of about −40° C. to about −78° C., and reprotonating the fatty acid with a strong acid.

18. The method of claim 16, wherein the lipase is an *Aspergillus niger* lipase and wherein at least 85% of the free fatty acid of conjugated linolenic is the c9,t11 isomer.

19. The method of claim 9, wherein the lipase is an *Aspergillus niger* lipase.

20. Conjugated fatty acid isomers made by the method of claim 8, the isomers comprising at least one isomer of a free fatty acid of conjugated linoleic acid, wherein at least 85% of the free fatty acid of conjugated linoleic is the c9,t11 isomer.

21. Conjugated fatty acid isomers made by the method of claim 19, the isomers comprising at least one isomer of a free fatty acid of conjugated linoleic acid, wherein at least 85% of the free fatty acid of conjugated linoleic is the c9,t11 isomer.

22. Conjugated fatty acid isomers made by the method of claim 16, the isomers comprising at least one isomer of a free fatty acid of conjugated linoleic acid, wherein at least 85% of the free fatty acid of conjugated linoleic is the c9,t11 isomer.

* * * * *